United States Patent [19]
Kim et al.

[11] Patent Number: 5,744,163
[45] Date of Patent: Apr. 28, 1998

[54] SUSTAINED RELEASE FORMULATION OF ANIMAL GROWTH HORMONE AND PROCESS FOR PREPARATION THEREOF

[75] Inventors: Ae-Ri Kim; Nam-Joong Kim; Min-Hee Jung, all of Daejeon, Rep. of Korea

[73] Assignee: LG Chemical Ltd., Seoul, Rep. of Korea

[21] Appl. No.: 749,912

[22] Filed: Nov. 13, 1996

[30] Foreign Application Priority Data

Jan. 10, 1996 [KR] Rep. of Korea .................. 96-341

[51] Int. Cl.$^6$ ........................................... A61K 9/14
[52] U.S. Cl. .................. 424/489; 424/457; 424/458; 424/468; 424/497
[58] Field of Search .................. 424/489, 499, 424/490, 457, 458, 468, 497; 528/271

[56] References Cited

U.S. PATENT DOCUMENTS

| 5,317,079 | 5/1994 | Domb et al. | 528/271 |
| 5,482,927 | 1/1996 | Maniar et al. | 424/499 |

Primary Examiner—Thurman K. Page
Assistant Examiner—William E. Benston, Jr.
Attorney, Agent, or Firm—Anderson, Kill & Olick, P.C.

[57] ABSTRACT

The present invention relates to a sustained-release formulation of an animal growth hormone and a process for preparation thereof, comprising a step to produce solid pellets by mixing an animal growth hormone and an excipient in accordance with a direct tabletting method and a step to coat the pellets with a film comprising a biodegradable polymer and a poloxamer. The thus obtained formulation has small initial drug release, and shows a continuous and uniform effect when administered. Further, the formulation of the present invention may be produced economically in a large scale.

10 Claims, 4 Drawing Sheets

SUSTAINED RELEASE FORMULATION OF ANIMAL GROWTH HORMONE AND PROCESS FOR PREPARATION THEREOF

FIELD OF THE INVENTION

The present invention relates to an animal growth hormone formulation which continuously releases an effective and steady amount of the hormone over a period of more than 1 week when implanted in an animal body.

BACKGROUND OF THE INVENTION

An animal growth hormone is a protein, and it is therefore decomposed and absorbed by digestive enzymes when orally administered by mixing with feed. In order to maintain an effective concentration of the hormone in blood, it must thus be administered by a non-oral method, e.g., intramuscular or subcutaneous injection.

Animal growth hormones can now be produced in a large scale by the DNA recombination techniques, and it has been demonstrated that porcine somatotropin produced by such techniques improves the feed efficiency and reduces the fat thickness of pig's back. However, the currently available daily injection formulation may not be suitable for treating a large number of pigs in a big farm. Accordingly, a sustained-release formulation, which does not require daily administration and does not release an excessive amount of the drug at the initial stage, may be most preferable for practical application.

U.S. patent application Ser. No. 4,863,736 discloses a formulation produced by coating all but one side of a solid pellet of porcine somatotropin prepared without the use of a binding agent. However, this formulation containing no binding agent has the problem of swelling caused by osmotic pressure when it contacts with water.

To solve the swelling problem, U.S. patent application Ser. No. 4,786,501 discloses a method which comprises making solid pellets having a reduced salt content by way of conducting, e.g., dialysis, and then, coating the two end sides of the pellets. While a uniform coating of all sides of a pellet can be scaled up by using a general coating machine, a partial coating of selected sides of a pellet is difficult to perform in mass-production.

European Patent No. 0 462 959 discloses a method for making solid pellets from porcine somatotropin and a copper complex, and then, coating them with an aqueous solution of polyvinyl alcohol. Because an animal growth hormone is a protein, a method for preparing a composition thereof must not involve conditions which may cause denaturation of the protein. Proteins are known to be unstable in aqueous solutions and may lose activity when they contact with water at a high temperature, but they are quite stable in anhydrous organic solvent [D. B. Volkin and C. R. Middaugh, *The effect of temperature on protein structure in Pharmaceutical Biotechnology*, Vol. 2; Stability of Protein Pharmaceuticals, Part A, p215–247].

Buonomo et al. and Klindt et al. have reported a miniosmotic pump containing a porcine somatotropin solution for the controlled release of somatotropin [Buonomo et al., *J. Animal Science*, 73: 1318–1326, 1995; Klindt et al., *J. Animal Science*, 70: 3721–3733]. In accordance with this method, the concentration of porcine somatotropin in blood may be maintained at an effective level for about 6 weeks, and as a result, the feed efficiency is improved and the amount of fat is reduced. However, this miniosmotic pump formulation is expensive and it must be surgically implanted.

Thus, a commercially viable sustained-release formulation has not yet been established, i.e., there continues to exist a need to develop a sustained-release formulation of an animal growth hormone.

SUMMARY OF THE INVENTION

Accordingly, it is an object of the present invention to provide a sustained-release formulation of an animal growth hormone which is capable of maintaining its effect over 1 week when administered, and a method for the preparation thereof which is free from the risk of denaturing the hormone and suitable for a mass-production.

In accordance with the present invention, a solid pellet containing a hormone and an excipient is coated with a film composed of a biodegradable polymer and a poloxamer (surfactant) to obtain a sustained-release formulation of an animal growth hormone. Further, there is provided a process for the preparation thereof comprising: tabletting a powder mixture of a hormone and an excipient to obtain solid pellets and coating the pellets with a solution containing a biodegradable polymer and a poloxamer.

DETAILED DESCRIPTION OF THE INVENTION

Figure 1:
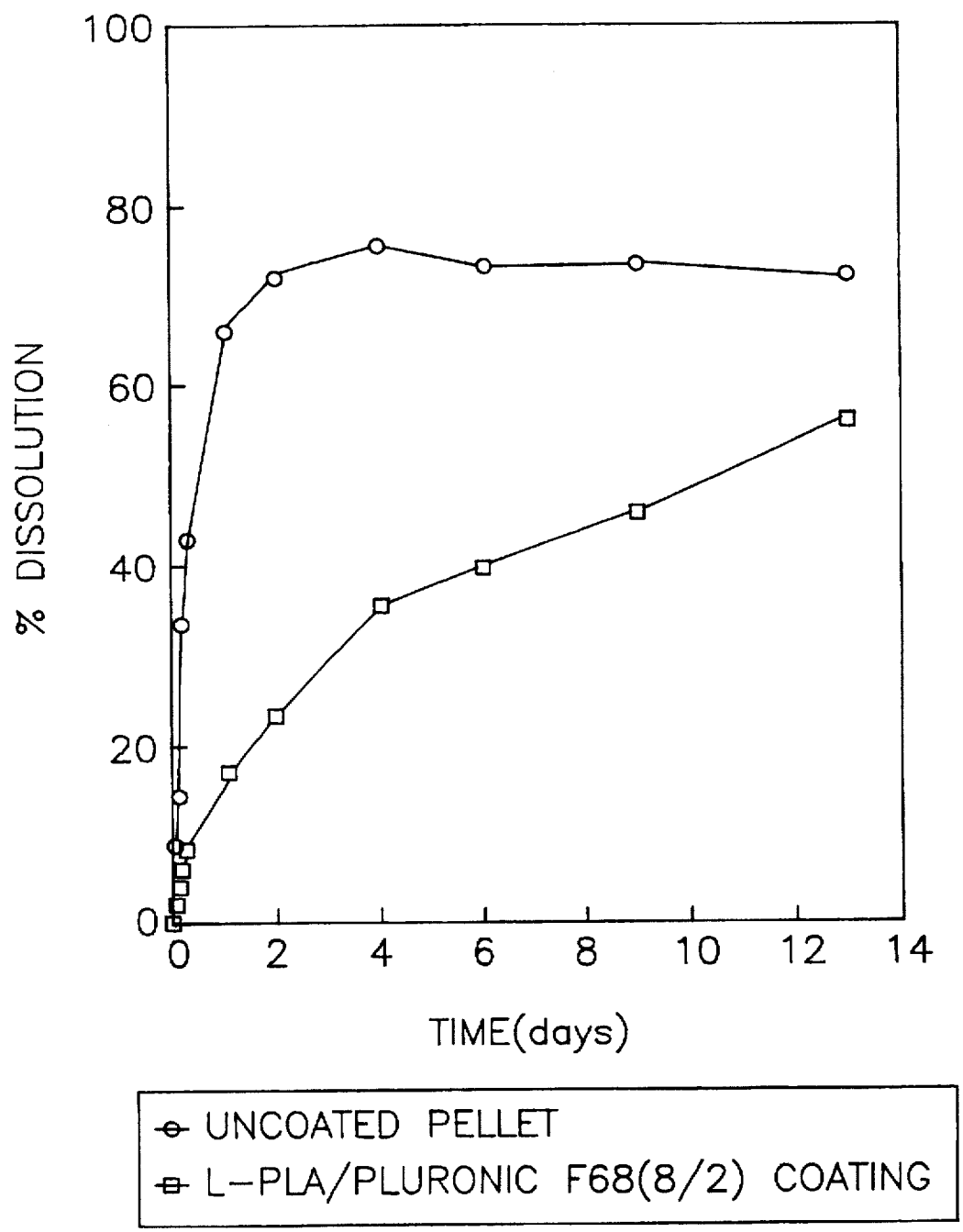
FIG. 1 compares the somatotropin dissolution curve of the pellets coated with a polymer film, prepared in accordance with the present invention, with that of uncoated pellets.

The formulation of the present invention is produced by coating a solid pellet, comprising an animal growth hormone and an excipient, with a film which is capable of regulating the rate of hormone release. The activity of the hormone may be preserved best in a solid formulation and this form is particularly suitable for mass-production wherein a conventional tabletting machine may be used.

The animal growth hormone suitable for use in the formulation of the present invention is bovine somatotropin or porcine somatotropin produced by DNA recombination techniques and the amount thereof may be preferably 20–80 wt % of the total weight of the formulation. The effective daily dosage of porcine somatotropin is known to be 100 µg/kg [*J. Anim. Sci.*, 68: 640–651(1990)]. A pig weighing over 70 kg requires about 7 mg/day of hormone, or about 100 mg of hormone for a 2 week hormone treatment.

A solid pellet formulation comprising a large amount of excipient is not suitable for practical use because of its large volume. On the other hand, a solid pellet containing no excipient may be small in volume, but has the problem of swelling, as was described previously [U.S. Pat. No. 4,863,736 and U.S. Pat. No. 4,786,501].

In the present invention, the amount of excipient is adjusted in the range of 20–80 wt % based on the total weight of the formulation. The excipient used in the present invention may play a role as a binding agent, which alleviates the problem of swelling, and also as a lubricating agent during the tabletting process. A hydrophilic or hydrophobic material may be used as an excipient. Exemplary hydrophilic excipients are water-soluble polymers which do not react with proteins, and these include water-soluble saccharides such as dextran, pectin, alginic acid, cellulose and the like; proteins such as gelatin; polyalkyleneglycols; and a mixture thereof. The most preferable hydrophilic excipient is polyethyleneglycol having a molecular weight ranging from 3500 to 35000. The formulation of the present invention may comprise said hydrophilic excipient in an amount ranging 0–80 wt % based on the total weight of the formulation.

On the other hand, exemplary hydrophobic excipients include waxes such as paraffin wax, carnauba wax, beeswax and the like; and water-insoluble proteins such as zein and ethylcellulose; among which paraffin wax is most preferred. The amount of the hydrophobic excipient may be preferably 0–80 wt % based on the total weight of the formulation.

The drug-release mechanism of the solid pellet formulation of the present invention may involve three steps. A hydration process occurs as the first step when the body fluid permeates into the formulation, and the rate of this process is determined by the hydrophilicity/hydrophobicity balance, the surface energy and the porosity of the formulation, among other factors. The next step is dissolution of the drug and this step is dependent mainly on the solubility and concentration of the drug. Finally the dissolved drug is released into body fluid by molecular diffusion, and this step may be influenced by the diffusivity of the drug, the drug concentration difference across the pellet boundary, the composition of the excipient and the like.

When the content of a hydrophilic drug in a solid formulation is over 20 wt %, or in some cases 10–15 wt % depending on the type of the drug used, drug particles are not isolated by the excipient but are interconnected to each other in a reticular form. When this formulation contacts with body fluid, the drug particles in the outer most part are dissolved, leaving behind a space for water filled channels to form. Subsequently, water permeates inside by capillary action and, as the drug particles get dissolved and released, new pathways for the next drug particle form.

Accordingly, when the hydrophilic drug content is large, the rate of the drug release is influenced not by the excipient, but by the rate of the drug diffusing through the pathways described above. Accordingly, the drug content may become one of the limiting factors in designing a sustained-release formulation. For example, U.S. patent application Ser. No. 4,761,289 discloses a sustained-release formulation comprising 25 to 75 wt % of bovine somatotropin. This formulation is prepared in a matrix form by using polymers such as polylactide, polycaprolactone, ethylvinylacetate and the like. However, release profiles of these formulations were not provided.

It is well known in the art that the rate of drug release may be controlled by using a polymer film. In the present invention, a solid pellet formulation having a high drug content is coated with a particular film to better control the rate of drug release, i.e., the inventive formulation has a film comprising a biodegradable polymer and a poloxamer.

U.S. patent application Ser. No. 5,342,622 discloses a peptide or protein implant coated with a swellable, permeable film made of a non-degradable addition polymer e.g., a copolymer of ethyl acrylate and methyl methacrylate (Eudragit E 30D). This formulation, however, is inferior to the formulation of the present invention, which comprises a coating of a biodegradable condensation polymer, in terms of, e.g., storage stability at 30° C. (see Test Example 3).

Biodegradable polymers suitable for use in the present invention include polylactide (PLA), polyglycolide (PGA), poly(lactide-co-glycolide) (PLGA) and a mixture thereof. A poloxamer is a non-ionic surfactant belonging to the class of polyoxypropylene-polyoxyethylene copolymers, and an exemplary poloxamer used in the present invention is poloxamer 188.

U.S. patent application Ser. No. 5,330,768 discloses a formulation obtained by dispersing drug microparticles in a matrix composed of a biodegradable polymer and a poloxamer. In this formulation, the poloxamer forms a gel structure which retards the rate of drug release, and therefore, as the poloxamer content increases, the rate of the drug release decreases.

In contrast, the rate of drug release becomes higher as the poloxamer content increases in the inventive formulation, because the water-soluble poloxamer component creates water filled channels in the film, helping the drug to diffuse therethrough. The weight ratio of a biodegradable polymer to a poloxamer in the film of the present invention may preferably range from 7:3 to 9:1.

The formulation of the present invention may be produced in a large scale by using a conventional tabletting machine. The denaturation of a protein drug may be prevented by employing a direct tabletting method which does not involve a wet granulation process often used in the conventional tabletting method. The wet granulation process, involving a prolonged contact with water and a drying process at a high temperature, is not suitable for moisture-sensitive drugs e.g., protein drugs. The direct tabletting method, on the other hand, does not require a separate granulating step, but instead employs a mixture of drug and excipient powders. In this method, the flow property and density of the drug/excipient powder mixture are important, and therefore, one must take proper care in selecting the excipient, mixing method, particle shape, particle size distribution and the like.

In the present invention, a bovine or porcine somatotropin powder obtained by a freeze-drying or spray-drying method may be used in an amount of 20–80 wt % based on the total weight of the formulation. The freeze-drying step does not cause denaturation of the protein, but the particles obtained thereby have irregular shapes as well as a wide size distribution. In contrast, spray-dried particles are nearly spherical in shape and show a relative narrow size distribution. However, the spray-drying method gives a maximum yield of only 70–80%. Accordingly, a suitable drying process may be selected based on consideration of the economics and the process variables.

An excipient having a desirable particle size is mixed with an animal growth hormone powder in a desired ratio according to a well-known method, e.g., ball-mill. The mixed powder is tabletted to obtain pellets of cylindric shape having a diameter of 2.5–4.5 mm and length of 2–6 mm. The above pellet size may be suitable for implantation using the conventional administering tools for animals, i.e., pigs and cows, without recourse to a surgical operation. However, the exact size and shape of the pellet may vary, depending on the amount of administered drug and other factors.

As to the coating step, a polymer coating solution may be sprayed on the pellets using a fluid-bed coating machine or a pan-coating machine. The film thickness may be adjusted based on the drug content, the desired rate of drug release and the like, and it ranges preferably from 10 to 50 μm. The temperature of the hot air used during the spray coating procedure must be so low as not to denature the proteins contained in the formulation, but higher than the vaporizing temperature of the solvent. The coated pellets may be dried preferably in a vacuum oven in order to remove the residual solvent.

The following Examples are given for the purpose of illustration only and are not intended to limit the scope of the invention.

EXAMPLE 1

Step 1) Preparation of a Pellet of Porcine Somatotropin by Direct Tabletting Method 10 g of paraffine wax and 10 g of polyethyleneglycol 35000 (PEG 35K) were passed through a 0.84 mm sieve and mixed with 20 g of freeze-dried recombinant porcine somatotropin powder (Korean Patent Application No. 86-11710) using a ball mill (Erveka) for 4 hours. The mixed powder thus obtained was formed into cylinder-shaped pellets having an average diameter of 3 mm and an average length of 6.5 mm by manually operating a tabletting machine (Korsh, EKO). An automatic tabletting operation was also attempted to produce pellets composed of polyethylene-glycol 35,000 (PEG 35K), carnauba wax and porcine somatotropin (PST) in a weight ratio of 1:1:2, and each pellet having an average weight, diameter and length of 54.8 mg, 4.0 mm and 4.6 mm, respectively.

The manually tabletted pellets are used in the following Examples.

Step 2) Preparation of Film-Coated Pellets

A coating solution was prepared by dissolving 0.33 g of PLA(L-PLA, Birmingham Polymer Inc.) and 0.084 g of poloxamer 188 (Pluronic F68, Fluka) in 4 ml of methylene chloride. The pellet obtained in step 1 was placed on a releasing membrane, wetted with a drop of the coating solution prepared above, and then, the excess coating solution was removed immediately. The coated pellet was dried in a hood for 1 hour and subsequently in a desiccator under a reduced pressure for 1 day.

EXAMPLE 2

A formulation of porcine somatotropin was prepared in accordance with the same method in Example 1 except that the ratio of L-PLA to Pluronic F68 was 9:1.

EXAMPLE 3

A formulation of porcine somatotropin was prepared in accordance with the same method in Example 1 except that the ratio of L-PLA to Pluronic F68 was 7:3.

EXAMPLE 4

12 g of L-PLA and 3 g of Pluronic F68 were placed in a bottle together with 300 ml of methylene chloride and 350 ml of acetonitrile, and the mixture was stirred to obtain a coating solution.

Light-yellow colored fake pellets composed of starch, carnauba wax and a food coloring agent in a weight ratio of 79:20:1 were produced in accordance with the procedure in Step 1 of Example 1.

1 kg of the fake pellets obtained above and fifty pellets of porcine somatotropin obtained in Step 1 of Example 1 were spray-coated with the coating solution prepared above using a Hi-Coater. The rate of fan rotation was 25 rpm; the air pressure was 1.5 kg/cm$^2$; the temperature of the influx air was 30° C.; and the spray rate of the coating solution was controlled at 20 ml/min by using a gear pump. The coated pellets were air dried for 30 min, and then, in a drying oven at below 0.001 torr and room temperature for 12 hours. The pale white pellets containing porcine somatotropin were separated from the fake yellow pellets.

COMPARATIVE EXAMPLE

A porcine somatotropin formulation was produced in accordance with the same procedure in Example 1 using a Eudragit suspension(Eudragit NE30D, Rohm Pharm tech) as a coating solution without dilution.

Test Example 1: Dissolution Test of the Formulation of Porcine Somatotropin

To each of two 40 ml glass vials, each containing 15 ml of phosphate buffered saline (pH 7.4), were added the uncoated pellets obtained in Example 1 and the coated pellets obtained in step 2 of Example 1, respectively. The vials were set in a shaker maintained at 37° C. and 100 rpm and 5 ml samples were taken at a fixed interval and each sampling was followed immediately by supplementing 5 ml of buffer solution. Standard porcine somatotropin solutions having concentrations of 0.1, 0.2, 0.5 and 1 mg/ml were prepared and their absorbances at 278 nm were measured with a spectrophotometer to obtain a standard calibration curve. The concentration of a sample was then calculated based on its absorbance relative to the standard.

FIG. 1 compares somatotropin dissolution curve of the pellets coated with polymer film with that of the uncoated pellets. The % dissolution represents the cumulative amount of the hormone eluted relative to the initial content of the hormone. As shown in FIG. 1, the released rate of the drug was remarkably slow with the coated pellet and the total amount of porcine somatotropin released by the coated pellet in 13 days was below 60%, whereas the uncoated pellet released more than 60% in one day. This result shows that the formulation of the present invention is suitable for a sustained-release formulation of porcine somatotropin.

Figure 2:
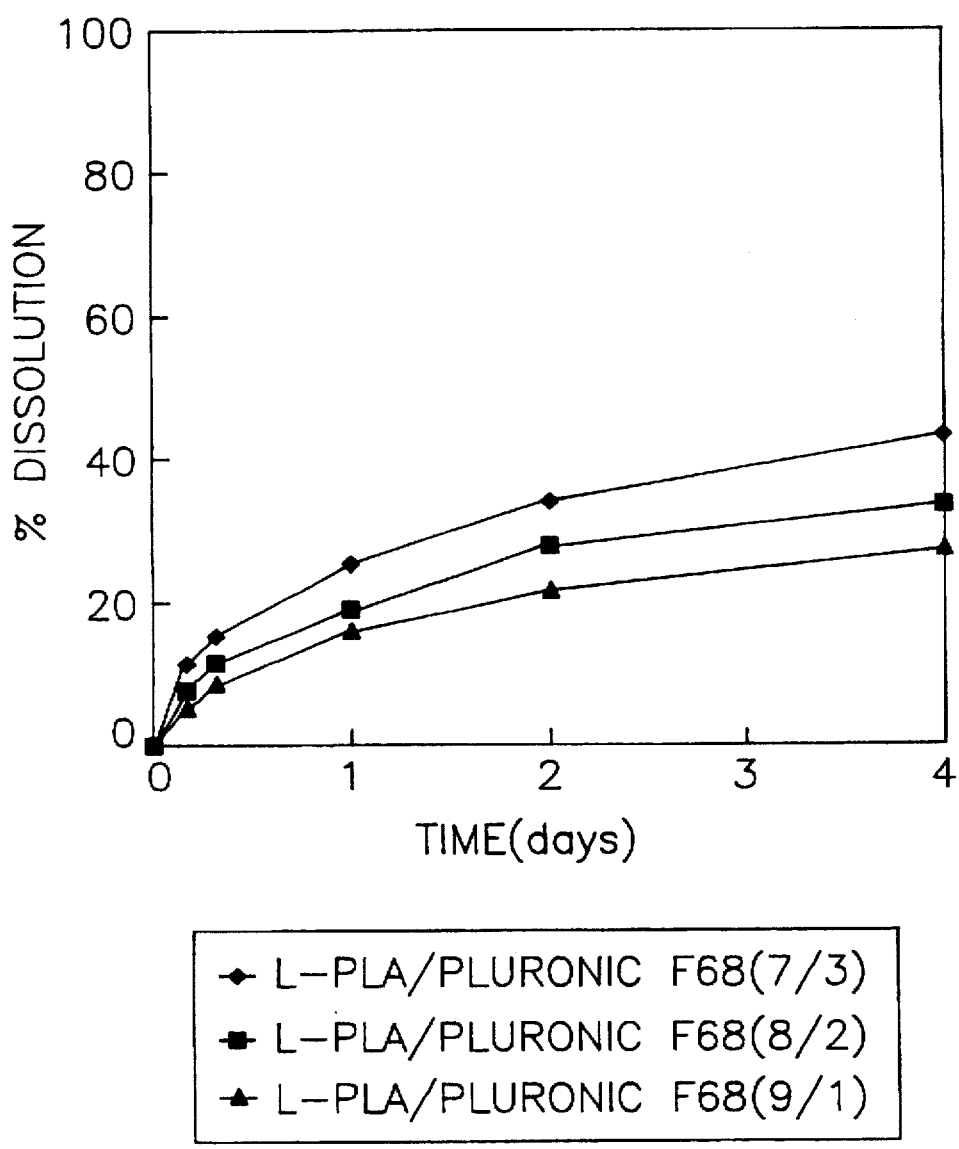
FIG. 2 shows the change in somatotropin dissolution from the inventive pellets depending on the constitution of the coating film.

Test Example 2: Dissolution Test according to the Constitution of Film on Formulation of Porcine Somatotropin The dissolution tests of the porcine somatotropin formulations obtained in Example 1 to 3 were conducted in accordance with the same procedure as in Test 1. The results in FIG. 2 show that as the poloxamer content of film increases, the dissolution rate increases.

Test Example 3: Effect of Formulation of Porcine Somatotropin on Weight Gain of Dwarf Rats and Stability of Formulation It is well known that an animal growth hormone, e.g., bovine somatotropin or porcine somatotropin brings about weight gain in rats [J. of Anim. Sci., 73:1019–1029, 1995]. Dwarf rats having the heredity of low growth hormone secretion were employed in a test to examine the effect of the porcine somatotropin formulation of the present invention.

First, for the purpose of evaluating the storage stability concurrently with the activity test, the coated formulations obtained in Example 4 and Comparative Example, and the uncoated formulation obtained in Step 1 of Example 1 were stored at 4° C. for 1 week in one case, and 30° C. for 1 month in the other. Identifying labels were attached to the tails of 8 weeks-old female dwarf rats, weighed for 3 days and those deviating far from the average weight were excluded so that a group of rats having a uniform weight distribution could be. After fixing the forefeet, hindfeet and the foreteeth of a rat, a 1 cm cut was made on the ventromedian line, a pellet was inserted into the hypoderm, and the incision was closed using a silk suture in accordance with a discontinuous suture method. After the implantation, they were weighed every day at a fixed time and compared with rats in a control group.

Figure 3A:
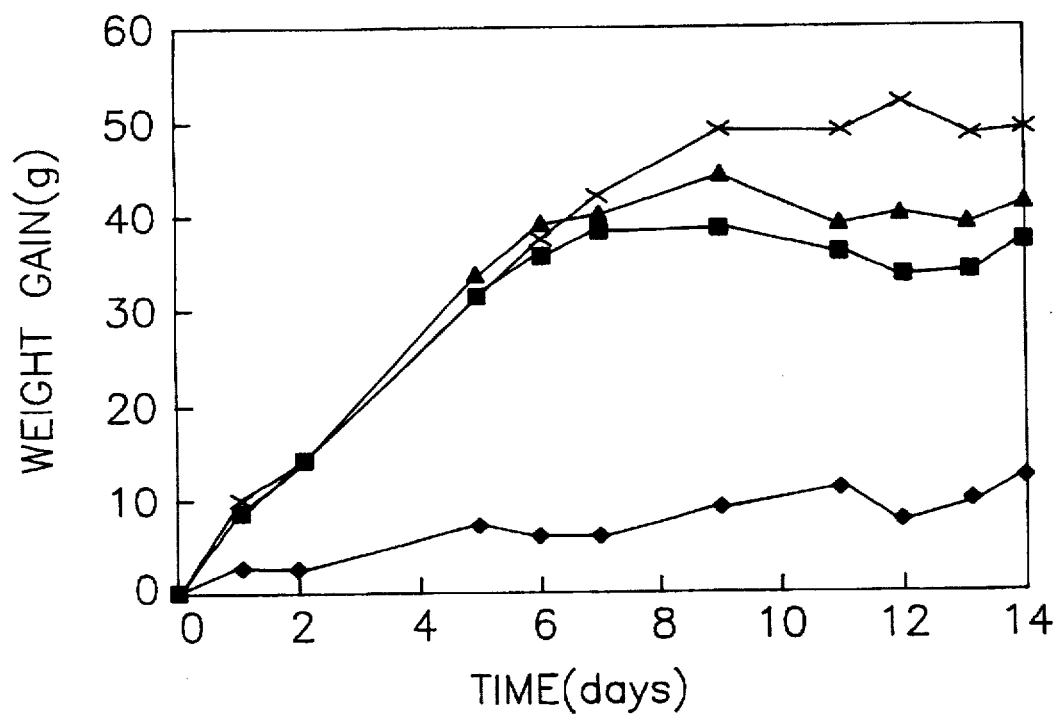
FIGS. 3a and 3b shows the effects on the weight of dwarf rats of administering various somatotropin formulations after storing at 4° C. for 1 week (FIG. 3a) or at 30° C. for 1 month (FIG. 3b).
Figure 3B:
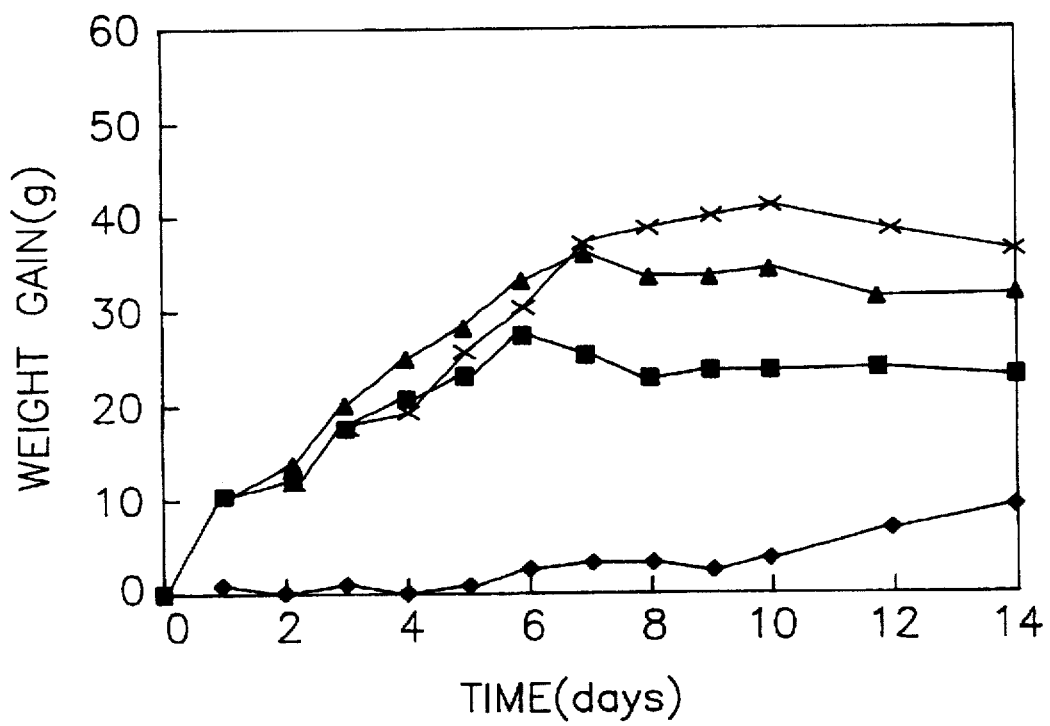

FIG. 3 shows the effects of the formulation of the present invention on the weight of dwarf rats. When the formulations were stored at 4° C. for 1 week and then administered to the rats, the results shown in FIG. 3a were obtained; the coated formulation of the present invention was superior over the uncoated formulation or the formulation coated with Eudragit NE30D in terms of the effect on the weight gain. Further, as the results obtained for formulation stored at 30° C. for 1 month show (FIG. 3b), the formulation of the present invention performed better than the other two formulations, i.e., it has a better storage stability.

While the invention has been described with respect to the specific embodiments, it should be recognized that various modifications and changes may be made by those skilled in the art to the invention which also fall within the scope of the invention as defined by the appended claims.

What is claimed is:

1. A sustained-release formulation of an animal growth hormone comprising a solid pellet containing an animal growth hormone and an excipient; and a film composed of a biodegradable polymer and a poloxamer, wherein said film coats said pellet, and wherein the biodegradable polymer is polylactide (PLA), polyglycolide (PGA), poly(lactide-co-glycolide) (PLGA) or a mixture thereof.

2. The formulation of claim 1, wherein the animal growth hormone is bovine somatotropin or porcine somatotropin.

3. The formulation of claim 1, wherein the amount of the animal growth hormone is 20–80 wt % based on the total weight of the formulation.

4. The formulation of claim 1, wherein the excipient is a hydrophilic or hydrophobic material, or a mixture thereof, and the amount thereof is from 20 to 80 wt % based on the total weight of the formulation.

5. The formulation of claim 4, wherein the hydrophilic material is polyethyleneglycol, dextran, pectin, alginic acid, cellulose, gelatin, or a mixture thereof.

6. The formulation of claim 4, wherein the hydrophobic material is paraffin wax, carnauba wax, bees wax, zein, ethylcellulose, or a mixture thereof.

7. The formulation of claim 1, wherein the film comprises a biodegradable polymer and a poloxamer in a ratio ranging from 7:3 to 9:1.

8. A process for the preparation of a sustained-release formulation of an animal growth hormone, which comprises; directly tabletting a powder mixture of an animal growth hormone and an excipient to obtain a solid pellet; coating the pellet with a film composed of a biodegradable polymer and a poloxamer.

9. The process of claim 8, wherein the animal growth hormone is spray-dried.

10. The process of claim 8, wherein the animal growth hormone is freeze-dried.

* * * * *